United States Patent [19]

Howarth

[11] Patent Number: 5,089,941
[45] Date of Patent: Feb. 18, 1992

[54] FLUX CONTAINMENT DEVICE

[75] Inventor: Robert F. Howarth, El Cajon, Calif.

[73] Assignee: The United States of America as represented by the Secretary of the Navy, Washington, D.C.

[21] Appl. No.: 579,004

[22] Filed: Sep. 6, 1990

[51] Int. Cl.⁵ .............................................. F21V 33/00
[52] U.S. Cl. .................................. 362/154; 362/310; 362/362; 356/243
[58] Field of Search ............... 362/154, 253, 257, 310, 362/359, 362; 250/505.1, 252.1; 356/243

[56] References Cited

U.S. PATENT DOCUMENTS

| | | | |
|---|---|---|---|
| 2,310,624 | 2/1943 | Eshey et al. | 362/310 |
| 2,321,080 | 6/1943 | Haber | 362/359 |
| 3,413,066 | 11/1968 | Biber et al. | 356/243 |
| 3,610,737 | 10/1971 | Bender | 250/505.1 |
| 3,648,056 | 3/1972 | Buttweller et al. | 250/239 |
| 3,699,471 | 10/1972 | Mulready et al. | 331/94.5 |
| 4,049,987 | 9/1977 | Helms | 250/505.1 |
| 4,344,668 | 6/1982 | Gunther et al. | 350/96.27 |
| 4,634,854 | 1/1987 | Wirick | 250/216 |
| 4,641,933 | 2/1987 | Blom | 350/613 |
| 4,772,102 | 9/1988 | Fergason et al. | 350/338 |

Primary Examiner—Ira S. Lazarus
Assistant Examiner—Sue Hagarman
Attorney, Agent, or Firm—Harvey Fendelman; Thomas G. Keough

[57] ABSTRACT

A flux containment device entraps an unneeded portion of the radiated energy emitted by a reference source lamp so that a determinable amount of radiation is projected to electro-optical sensors for calibration purposes. A double-walled, concentric can-shaped enclosure, provided with a nonreflective coating on its inside surfaces, has an aligned calibration optical axis aperture for projecting the determinable amount of radiation and a diametrically opposed light trap opening to accommodate a light trap that eliminates unwanted reflections. The double walls are held apart by nonconductive spacers to avoid unwanted heat transfer. A fan forces cooling air through an appropriately located vent hole in the can-shaped enclosure to avoid direct impingement on the lamp. One end of the can-shaped enclosure is provided with a disc-shaped baffle having appropriate spacing and openings to permit the flow of cooling air from the fan and the opposite end is appropriately shaped to accommodate a mounting surface, such as, for example, a lathe bed bench structure.

8 Claims, 1 Drawing Sheet

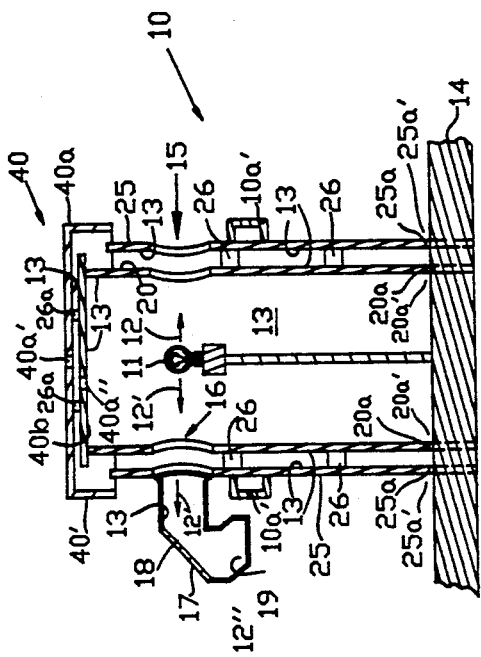
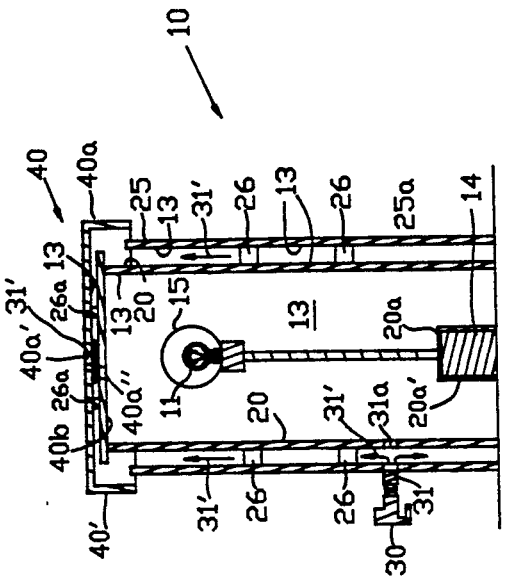
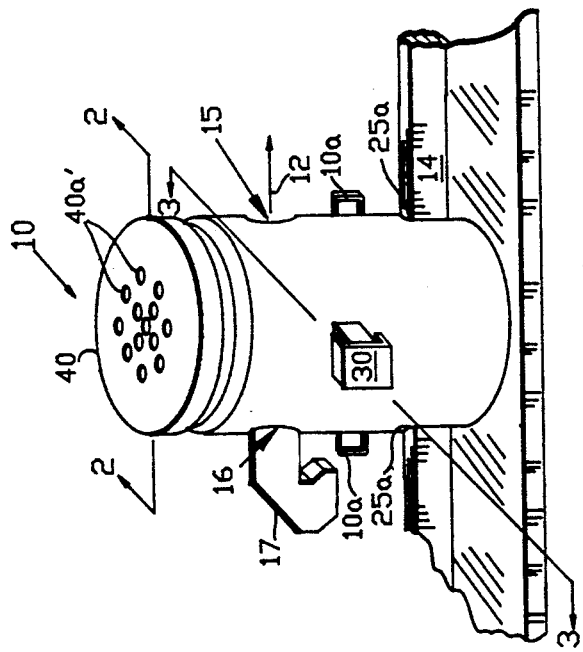

FLUX CONTAINMENT DEVICE

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The ongoing emergence of the use of optical means for collecting, transmitting and processing information emphasizes an acute need for a reliable and accurate calibration of components for effective information transfer. The accurate calibration of a wide variety of optical sensors must precede their applications so that meaningful data can be collected.

Historically, such sensors usually are calibrated at a fixed and permanent manufacturing facility or in a centralized calibration laboratory. This may mean that some time may pass before their ultimate deployment, irrespective that time, intervening events and ambient exposures might alter some components' responses prior to use.

At least one conventional calibration approach using curtains attempted to prevent unneeded and unwanted radiant energy from reaching the sensors under calibration. The bulky, opaque black curtains and adjustable baffles were placed around a reference source which irradiated the sensors undergoing calibration and test. The opaque curtains were heavy to provide light containment and to eliminate extraneous light reflection paths caused by the walls, floor, ceiling and other neighborhood objects. The curtains also were needed to block direct vision paths to protect the workers' eyes. Although the potentially unsafe direct vision paths were reduced, sometimes the curtain structure allowed for numerous unforeseen paths of opportunity for unwanted exposure due to the displacable geometry of the curtain arrangement. Furthermore, associated curtain supporting structure, such as, hangers, rails, ropes and hooks were needed which allowed worker access to the calibration elements. All this paraphernalia restricted worker movement. Thus, the technique, while arguably being effective, imposed the disadvantages of bulk, restriction of worker movement and the ever-present danger of exposing the worker's eye's to the intense tungsten filament lamp output (up to 1000 watts).

Thus, a continuing need exists in the state of the art for a man-portable device that eliminates curtains and the associated paraphernalia to increase worker safety by reducing the possibility of direct vision paths to an intense calibration light while attaining a desired suppression of stray light and increased worker accessibility to enable a more accurate calibration.

SUMMARY OF THE INVENTION

The present invention is directed to providing an apparatus for containing extraneous flux radiated from a lamp projecting a reference level of energy. A housing having an internal nonreflective surface is sized to contain the lamp and is provided with an optical calibration axis aperture for projecting the reference level of energy and a light trap opening aligned with the lamp and aperture. A light trap is mounted to enclose said light trap opening and thereby prevent any 180° reflections of the extraneous flux from being projected with the reference level of energy. A fan introduces cooling air into the housing, but not directly impinging on the lamp to assure reliable operation. Sheet metal fabrication of the housing from can-shaped spaced-apart coaxial inner and outer shells and a disc-shaped cover, helps provide a man-transportable structure that reduces hazards, such as the possibility damage to the eyes or of burns.

An object of the invention is to provide a flux containment device used to entrap the extraneous flux from a lamp projecting a reference level of energy for calibration purposes.

Another object is to provide a man-transportable calibration apparatus that does not expose operating personnel to radiation hazards or expose them to hot surfaces.

Another object is to provide a flux containment device suitable for prolonged operation by inclusion of cooling which does not compromise radiation effectiveness.

Another object is to provide a flux containment device of convenient size that allows freedom of operation with safety and easily attains suppression of stray light flux.

Another object is to provide a flux containment device having a double-shell construction to provide a nearly complete containment of lamp flux and a cool surface safe to the touch.

These and other objects of the invention will become more readily apparent from the ensuing specification and drawings when taken in conjunction with the appended claims.

BRIEF DESCRIPTION OF THE DRAWINGS

FIG. 1 is an isometric depiction of the flux containment device operationally disposed.

FIG. 2 shows a cross-sectional view of the device taken generally along lines 2—2 in FIG. 1.

FIG. 3 is a cross-sectional depiction of the invention taken generally along lines 3—3 of FIG 1.

DESCRIPTION OF THE PREFERRED EMBODIMENT

Referring now to the drawings, a flux containment device 10 has been specifically designed to entrap the unneeded and extraneous flux radiated from a lamp 11 projecting a reference level 12 of energy through a calibration optical axis aperture 15. This reference level of energy is used to calibrate various optical sensors and other optical data devices, not shown, that are becoming of increasing importance in a wide variety of optical date processing applications. This structure to be described avoids many of the limitations which have otherwise been called into play during the calibration process.

The flux containment device encloses lamp 11 which is a radiometric calibration source for calibrating various light-measuring devices. The lamp may be a tungsten iodide (halogen) lamp operating, for example, at 2800 degrees Kelvin. Such a lamp functions as a broadband source, sometimes referred to as a gray body with a spectral characteristic extending from, for example, 250 nanometers to 2,500 nanometers (2.5 microns) and, among other lamps, has been used as a reference standard source for calibrating a large variety of associated optical devices. Use of such lamps always should be with caution since their intense radiations pose hazards to operating personnel. A relatively cumbersome optical baffle arrangement, such as curtains and support structure, otherwise has been required to prevent eye contact and unwanted reflections from reaching the components being calibrated.

Referring now to FIGS. 2 and 3, device 10 is formed of a pair of can-shaped, coaxial double-shell circular cylinders 20 and 25. The inner and outer cylindrical shells are mechanically held in the coaxial relationship by a number of screws, not shown, which engage threaded ceramic spacers 26 so that a free space is provided between the shells to permit air flow from a cooling fan 30.

Cooling fan 30 is mounted on the exterior of outer shell 25 to direct the passage of a cooling gas, such as air, through a cooling vent hole 31 provided in outer cylindrical shell 25. Cooling vent hole 31 and the orientation of cooling fan 30 are such as to direct the cooling gas along the outer surface of inner shell 20, see gas flow arrows 31' in FIG. 3, and prevent a heat build up in the flux containment device. Optionally, the cooling vent hole may extend through both shells in a supplemental cooling vent hole 31a; however, care must be taken that the direct flow of cooling air does not directly impinge upon lamp 11. Direct impingement of the cooling gas on the lamp may change its temperature and its spectral emittance so that a calibration may be faulty. The single shell vent hole design helps assure that the cooling air circulates about the shells for better cooling and that the flow of cooling gases does not directly impinge on the lamp.

An essentially disc-shaped cover 40 has a double-wall construction 40a and 40b that is mechanically held in a coaxial spaced apart relationship by a number of screws, not shown, which engage threaded ceramic spacers 26a to allow the passage of the cooling gas from the flux containment device via holes 40a'. Cover 40 is also held by spacers 26a in a slightly spaced-apart relationship with respect to the inner and outer cylindrical shell to allow the passage of the cooling gas from the interior which surrounds lamp 11.

A light trap opening 16 is provided through can-shaped, coaxial double-shell circular cylinders 20 and 25 in a coaxially aligned disposition with respect to optical calibration axis aperture 15 and lamp 11. A light trap 17 is mounted on outer shell 25 and includes a mirror 18 disposed at a 45 degree angle with respect to the optical calibration axis established by the lamp and the optical calibration axis aperture.

Mirror 18 reflects the 180° component 12' of light from lamp 11 into a fuzzy felt-like material 19 in light trap 17. Component 12' is referred to as the 180° component since it is going in the opposite direction with respect to the direction of the desire reference level of energy. The mirror and fuzzy 14 felt like material thereby prevent component 12' from being reflected back in the direction of the desired reference level along the optical calibration axis toward the component to be calibrated and to be added to reference level 12. A reflection from component 12' could provide an indeterminable level of unwanted light for calibration that would be different than the magnitude of the desired reference level. For this reason, it is essential that component 12' be absorbed in material 19.

The bottom ends of the inner and outer cylindrical shells are appropriately shaped 20a and 25a to accommodate a mounting surface such as, for example, a lathe bed bench 14. A resilient or felt-like black material 20a' or 25a' can be provided to assure that no extraneous light enters or leaves the flux containment unit.

All of the internal surfaces of flux containment device 10 are provided with a nonreflective surface 13. This can be a flat, black nonreflective paint, a suitable anodizing or other nonreflecting textured coating or surface. The flux containment device with its nonreflective surface plus the aligned trap hole 16 with material 19 and materials 20a' and 25a' prevent reflections and keep extraneous light out.

Since the inner and outer cylindrical shells are fabricated from a rolled sheet metal such as steel, the unit is man-transportable to enable it being relocated. Handles 10a' on opposite sides facilitate this relocation capability. In addition, the metal fabrication aids the cooling of the structure so that lamp 11 does not appreciably change spectral output.

The double surface provided by inner and outer cylindrical shells 20 and 25, as well as the inner and outer disc cover surfaces 40a and 40b of disc cover 40, covers the lamp. A number of nonaligned vent holes 40a' and 40a'' provided in the two disc cover surfaces optionally are included to aid the airflow. Optionally a turned-down rim 40' of disc cover 40 may aid in light flux blocking, especially if it is made to extend below the top of cylinder 25. In this case, the outside diameter of 40' must exceed that of cylinder 25 in order to permit the cooling air exhaust and to aid in the light flux blocking. The air-moving fan 30 mounted on the outer shell 25 below the calibration axis provides moderate air movement between the cylindrical shells and around the lamp but does not blow directly on the lamp. In this manner much of the heat generated by the lamp is carried out between the shell structure of the flux containment device without affecting the lamp. The thermal isolation provided by the ceramic spacers 26 and 26a and the gas movement by the fan helps assure that the outer surfaces of flux containment device are cool to the touch and operators are not burned by the high intensity lamp's radiation. The complete enclosure of the lamp also assures that the hazards associated with the lamp's intensity does not reach technicians' eyes.

The near complete containment of lamp flux and the cool surface provided by the flux containment device assures that the attention of workers can be directed to the task at hand. Since the enclosure is lightweight and easy to lift up and away to provide access to the lamp, appropriate changes can be made when warranted. The handles, diametrically opposed on the external surfaces of outer cylindrical shell 25, greatly reduce the effort that might otherwise be associated with gaining access to a lamp.

Obviously, many modifications and variations of the present invention are possible in the light of the above teachings. It is therefore to be understood that within the scope of the appended claims, the invention may be practiced otherwise than as specifically described.

What is claimed:

1. An apparatus for containing extraneous flux radiated from a lamp projecting a reference level of energy comprising:
   a housing sized to receive said lamp therein being provided with an internal nonreflecting surface and being further provided with an optical calibration axis aperture for projecting said reference level of said energy therefrom and a light trap opening, said optical calibration axis aperture and said light trap opening being aligned with said lamp;
   a light trap mounted on said housing to enclose said light trap opening, to prevent 180 degree reflections of said extraneous flux from being projected with said reference level of said energy.

2. An apparatus according to claim 1 in which said housing is provided with a vent hole and further including:
a cooling fan mounted with respect to said vent hole in said housing to bring cooling gas therein in a manner so as to avoid direct impingement on the lamp.

3. An apparatus according to claim 2 in which said housing is cylindrically shaped and said optical calibration axis aperture and said light trap opening are diametrically opposed thereon.

4. An apparatus according to claim 3 in which said housing is a can-shaped double-shell right circular cylinder with a disc cover, the inner shell and the outer shell of said can-shaped double-shell right circular cylinder are separated by shell spacers and said optical calibration axis aperture and said light trap opening are provided in both said inner shell and said outer shell in an aligned relationship and said vent hole extends through at least said outer shell.

5. An apparatus according to claim 4 in which said disc-shaped cover is mounted on a top end of said can-shaped double-shell right circular cylinder by cover spacers to permit the passage of said cooling gas.

6. An apparatus according to claim 5 in which said can-shaped double-shell right circular cylinder has a bottom end shaped to fit over a calibration fixture structure to block the passage of said extraneous flux.

7. An apparatus according to claim 6 in which said inner shell, said outer shell and said disc cover are fabricated from a metal sheet material to provide a man-transportable structure, said inner shell, said outer shell, said disc cover, said shell spacers and said cover spacers reduce the hazards of inflicting burns to an operator.

8. An apparatus according to claim 7 further including:
a pair of handles connected to said outer shell to assure said man-transportable structure.

* * * * *